United States Patent [19]
Yates et al.

[11] Patent Number: 5,190,626
[45] Date of Patent: Mar. 2, 1993

[54] PROCESS FOR REMOVING VINYLIDENE CHLORIDE AND OTHER UNSATURATED COMPOUNDS FROM 1,1-DICHLORO-1-FLUOROETHANE

[75] Inventors: Stephen F. Yates, Arlington Hts., Ill.; Addison M. Smith, Amherst, N.Y.; Arthur F. Murphy, Mt. Arlington, N.J.

[73] Assignee: Allied-Signal Inc., Morris Township, Morris County, N.J.

[21] Appl. No.: 627,070

[22] Filed: Dec. 13, 1990

[51] Int. Cl.$^5$ .............................................. C07C 17/00
[52] U.S. Cl. ........................... 204/157.95; 204/158.20; 204/158.21
[58] Field of Search ................. 204/157.95, 158.21, 204/158.20, 157.95

[56] References Cited

U.S. PATENT DOCUMENTS

| | | | |
|---|---|---|---|
| 2,707,197 | 4/1955 | Souillard | 204/158.21 |
| 2,945,796 | 7/1960 | Seller | 204/158.21 |
| 3,629,085 | 12/1971 | Coppens | 204/158.21 |
| 4,941,957 | 7/1990 | Zeff et al. | 204/158.2 |
| 5,095,158 | 3/1992 | Bolmer | 570/180 |

FOREIGN PATENT DOCUMENTS 970344  9/1964  Fed. Rep. of Germany .................. 204/157.94

*Primary Examiner*—W. Gary Jones
*Assistant Examiner*—Dean Nguyen
*Attorney, Agent, or Firm*—Harold N. Wells; Jay P. Friedenson; Mary Jo Boldingh

[57] ABSTRACT

Vinylidene chloride is removed from 1,1-dichloro-1-fluoroethane (HCFC-141b) by contacting the HCFC-141b in the vapor phase with chlorine in the presence of ultraviolet light providing an exposure up to about 50 watts-hour/kg.

6 Claims, No Drawings

PROCESS FOR REMOVING VINYLIDENE CHLORIDE AND OTHER UNSATURATED COMPOUNDS FROM 1,1-DICHLORO-1-FLUOROETHANE

BACKGROUND OF THE INVENTION

This invention relates to the purification of 1,1-dichloro-1-fluoroethane, also designated HCFC-141b, which has been of particular interest as a replacement for chlorofluorocarbons having similar physical properties, particularly HCFC-11 and -113. HCFC-141b may be prepared by reaction of vinylidene chloride or trichloroethane with HF. Such processes are disclosed, for example, in U.S. Pat. Nos. 2,894,044 and 3,833,676.

It is characteristic of such reactions that many by-products are formed, containing varying numbers of hydrogen, chlorine, and fluorine atoms on methane, ethane, and ethylene molecules. These by-products and the unreacted feed material may be separated by distillation where possible. Some compounds are relatively harmless since their presence does not greatly alter the physical properties for which HCFC-141b is useful. Vinylidene chloride has a boiling point close to that of HCFC-141b making it difficult to separate them by distillation. Since vinylidene chloride is toxic, it must be removed from HCFC-141b. After distillation of the crude product, vinylidene chloride will still be present in amounts from about 500 to 1,200 ppm (wt.). It should be reduced to below 500 ppm according to the specifications of the Panel for Advancement of Fluorocarbon Test (PAFTII). Preferably, the vinylidene chloride should be below about 200 wt. ppm.

Dichloroacetylene is another toxic impurity. It may be present in crude HCFC-141b in amounts of about 5 to 25 ppm (wt.) and should be removed to below 1 ppm to meet the specifications referred to above.

Various methods have been suggested for removing vinylidene chloride and dichloroacetylene from waste streams. For example, in U.S. Pat. No. 4,940,824 it is shown that vinylidene chloride can be removed from HCFC-141b using carbon molecular sieves and in U.S. Pat. No. 4,940,825 that dichloroacetylene also can be removed from HCFC-141b or from vinylidene chloride.

In U.S. Pat. No. 4,948,479 Brooks et al. disclose the use of photochlorination to convert unsaturated carbon compounds, including vinylidene chloride from HCFC-141b. The patentees limit their process to photochlorination in the liquid phase and appear to infer that similar vapor phase photochlorination was known. However, while it is true that photochlorination of vinylidene chloride has been studied by Ayscough et al., Trans. Faraday Soc. 62(7) 1838–45(1966), and photochlorination of other unsaturated and chlorinated hydrocarbons have been reported, as Brooks et al. have discussed, it appears that the vapor phase photochlorination of unsaturated compounds, and particularly vinylidene chloride has not been disclosed to be an effective method of removing vinylidene chloride from HCFC-141b. It should be noted that the vapor phase photochlorination studies of Ayscough et al. involved below atmospheric pressure conditions with only vinylidene chloride and chlorine present, except where inert gases were introduced. Generally, the partial pressure of vinylidene chloride was higher than in the present process and since no other reactive species were present (e.g. HCFC-141b) one would not conclude from the results achieved in such a simplified model system that when large amounts of reactive species were present that vinylidene chloride could be selectively photochlorinated.

If possible, the use of vapor phase chlorination would present advantages, particularly since the purification steps are simplified, many of which can be carried out in the vapor phase, thus eliminating the need to condense and distill HCFC-141b before chlorination and then to vaporize it again for removal of acid gases. However, one skilled in the art might conclude from the available information that reducing the small amount of vinylidene chloride present in HCFC-141b by photochlorination could be unprofitable since extremely high selectivity would be required to chlorinate vinylidene chloride at low concentrations in HCFC-141b without chlorinating the HCFC-141b as well and vapor phase free radical chlorination would not be expected to be very selective. However, we have now found that vapor phase photochlorination is a suitable procedure for achieving low levels of vinylidene chloride and other unsaturated compounds when combined with other steps in a process for purification of crude HCFC-141b.

SUMMARY OF THE INVENTION

Vinylidene chloride is removed from a mixture consisting substantially of 1,1-dichloro-1-fluoroethane (HCFC-141b) and containing up to about 2000 wt. ppm vinylidene chloride by contacting the HCFC-141b mixture with 1-6 mols of chlorine for each mol of vinylidene chloride in the vapor phase in the presence of ultraviolet light having a wave length between about 300 to 400 nm which provides up to about 50 watts-hour/kg of the mixture. The vinylidene chloride can be reduced to below 200 wt. ppm, even to below 10 wt. ppm, as it is converted to 1,1,1,2-tetrachloroethane, which has a higher boiling point and can be easily separated from HCFC-141b. Other unsaturated compounds are also removed by chlorination to other derivatives which can be separated.

It is a feature of the process of the invention that the HCFC-141b can contain up to about 4 wt. % of 1-chloro-1,1-difluoroethane (HCFC-142b) without formation of no more than about 20 wt. ppm of the undesirable 1,2-dichloro-1,1-difluoroethane (HCFC-132b).

The UV light exposure used in the process of the invention is lower than heretofore suggested and preferably is about 0.05 to 50 watts-hour/kg. The process may be carried out at temperatures of about 0 to 100° C. and pressures which maintain the HCFC-141b in the vapor phase.

DETAILED DESCRIPTION OF THE INVENTION

While HCFC-141b produced by reacting vinylidene chloride or trichloroethane with HF over a catalyst will contain a variety of byproducts such as $C_4H_5F_5$(R-365), $CF_2ClCH_3$(R-142b), $CCl_2=CH_2$(R-1130a), $CCl_3CH_3$(R-140a), $CFCl=CH_2$ (HFC-1131a), it is of particular importance to remove vinylidene chloride and dichloroacetylene from the crude product. Preliminary separation of HCFC-141b by distillation will leave about 500 to 1,200 wt. ppm of vinylidene chloride and about 5 to 25 wt. ppm of dichloroacetylene. In the process of the invention, these and other unsaturated compounds are reacted with chlorine to provide more highly chlorinated compounds which have a higher boiling point and can be readily separated from HCFC-141b. At the same time the loss of the principal component HCFC-141b to HCFC-131a is minimal.

In U.S. Pat. No. 4,948,479 the patentees emphasized that it was important to reduce the amount of 1-chloro-1,1-difluoroethane (HCFC-142b) to below 100 ppm since it can be converted to 1,2-dichloro-1,1-difluoroethane (HCFC-132b), which is toxic and must be minimized in the final HFC-141b product. In their Example 1 the patentees show that in a feed containing about 300 ppm (wt.) of HCFC-142b that some HCFC-132b was made. We have now found that when crude HCFC-141b is photochlorinated in the vapor phase under the conditions of the invention, that no HCFC-132b was detected (that is, below about 1 wt. ppm) making it unnecessary to remove HCFC-142b. Even when the HCFC-142b content was up to about 4 wt. % in HCFC-141b, only minimal amounts of HCFC-132b were found (say up to about 20 wt. ppm).

Process Conditions

In our process, crude HCFC-141b containing about 500 to 1200 wt. ppm of vinylidene chloride and about 5 to 25 wt. ppm of dichloroacetylene along with minor amounts of other byproducts such as those mentioned above will be contacted in the vapor phase with chlorine in the presence of ultraviolet light having a wavelength of about 300 to 400 nm. It should be understood that an ultraviolet lamp may have radiation outside this range also, but that photochlorination requires UV light within this range.

The ultraviolet light will have an intensity which provides an exposure greater than zero and up to about 50 watts-hour/kg of the HCFC-141b mixture, preferably 0.05 to 50 watts-hour/kg, which is significantly lower than that used in U.S. Pat. No. 4,948,479 where the HCFC-141b was photochlorinated in the liquid phase. As a consequence of this reduced light intensity it has been found possible to tolerate significant amounts of 1-chloro-1,1-difluoroethane (HCFC-142b) since little or no 1,2-dichloro-1,1-difluoroethane (HCFC-132b) has been detected (that is, less than 20 wt. ppm).

The ultraviolet light may be provided by arc lamps including mercury, argon, or xenon and filament lamps including tungsten and halogen.

Chlorine is introduced into the HCFC-141b stream at a rate sufficient to provide about 1 to 6 mols of chlorine for each mol of vinylidene chloride.

It has been found that increasing either the ratio of chlorine to vinylidene chloride ($Cl_2$/VC) or the ultraviolet light exposure improves the chlorination of vinylidene chloride. Generally, we have been able to reduce the vinylidene chloride to below 200 ppm using a UV exposure above about 8 watt-hr/kg but with very low ratios of $Cl_2$/VC. Conversely, much lower UV exposures can be used if higher $Cl_2$/VC ratios are used. Table D below illustrates that the $Cl_2$/VC ratio and UV exposure may be adjusted to provide a desirable set of conditions. It has been found possible to reduce the concentration to below 10 wt. ppm when desired to do so.

The temperature employed may vary but may be from about 0° C. to 100° C., preferably about 21° to 100° C.

The pressure selected will be a convenient value to suit the processing conditions for HCFC-141b and will maintain HCFC-141b with vapor phase at the selected temperature.

The UV radiation from a lamp ordinarily will be expressed as watts, which is a rate of delivering energy. For present purposes, it is considered more useful to express radiation as the quantity of energy delivered over a period of time, i.e. the "exposure," rather than as the rate. Thus, the exposure may be expressed as watts-hours, which is related to the number of photons of energy delivered and their wavelength and these, in turn, relate to the chlorination of unsaturated molecules such as vinylidene chloride. Since the exposure is the product of the rate of delivering energy (photons/time) and the time, it will be clear that either the rate or the time could be varied. However, for practical applications the rate and the time will have limits imposed by the need to carry out the desired photochlorination reaction within constraints of time and product yield. If a high rate or a long time is used, not only will vinylidene chloride be chlorinated to 1,1,1,2-tetrachloroethane, but chlorine will react with other molecules, particularly with HCFC-141b to make HCFC-131a and with HCFC-142b to make HCFC-132b. Alternatively, if a very low rate or a short time is used, then insufficient chlorination of vinylidene chloride would be expected. In U.S. Pat. No. 4,948,479 Brooks et al. recommended an exposure of 1000 to 3000 watts-hour/kg. in their liquid phase photochlorination. In contrast, in our vapor phase photochlorination much lower exposures are required, only up to 50 watts-hour/kg. The use of reduced exposure to UV radiation provides many advantages, but would not have been expected to have been effective for removing small amounts of vinylidene chloride based on the Brooks et al. disclosure.

After the HCFC-141b has been photochlorinated, the chlorinated products may be separated from the HCFC-141b, as, for example, by distillation, since the boiling points are no longer close to that of HCFC-141b. Any residual chlorine, HCl or HF may be separated by absorption of chlorine in aqueous caustic, by adsorption on carbon molecular sieves, or reaction with aqueous sodium sulfite or sodium thiosulfate.

EXAMPLE 1

The photochlorination of HCFC-141b was carried out in a 60-mL quartz Griffith-Worden pressure vessel fitted with a water jacket through which 55° C. water was passed. The reactor vessel was placed at the focus of RPR-100 Rayonet reactor (Southern New England Ultraviolet Company) equipped with 12 RPR-3500 lamps having their peak intensity at a wavelength of 350 nm. Light below 300 nm was removed by a pyrex filter. Ferrioxalate actinometry was used to measure the radiation received (see *The Chemists Companion*, A. J. Gordon & R. A. Ford, Wiley Interscience (1972), pages 362–368). In this vessel under these conditions this procedure gave an incident light intensity of $1.416 \times 10^{-6}$ einstein/sec (0.482 watts).

Two feed streams were passed through separate lengths of capillary tubing heated to 60° C. and then mixed and passed into the reactor at 135 kPa. The impure HCFC-141b contained 1800 wt. ppm vinylidene chloride plus other impurities as listed below. One stream contained no chlorine while the second contained 0.106 mol of chlorine per kg of HCFC-141b. By blending the two streams the ratio of chlorine to vinylidene chloride was varied. The radiation exposure was calculated from the residence time and the light intensity. After exposure to the ultraviolet light the product stream was condensed and analyzed by gas chromatography.

The results of three tests are given in the table below. The compounds are designated as refrigerants (R) according to the commonly used system of the American Society of Refrigerating Engineers.

TABLE A

| Parameter | Feed | Sample 1 | Sample 2 | Sample 3 |
|---|---|---|---|---|
| $Cl_2$/V.C. molar ratio | — | 4.08 | 4.54 | 5.26 |
| Residence time (sec) | — | 11.78 | 12.55 | 6.07 |
| Exposure (w hr/kg) | — | 4.52 | 4.81 | 2.33 |
| Analytical Results | | | | |
| R-1131a | <10 ppm | <10 ppm | <10 ppm | <10 ppm |
| R-142b* | 3.5% | 0.1% | 235 ppm | 381 ppm |
| R-365 | 109 ppm | 124 ppm | 107 ppm | 138 ppm |
| R-1353 | <10 ppm | <10 ppm | <10 ppm | <10 ppm |
| Vinylidene chloride (R-1130a) | 1800 ppm | 363 ppm | 13 ppm | <10 ppm |
| R-140a | 133 ppm | 152 ppm | 155 ppm | 212 ppm |
| R-132b | N.D. | N.D. | N.D. | N.D. |
| R-151a | 5 ppm | 5 ppm | N.D. | N.D. |
| R-131a | N.D. | 5557 ppm | 7383 ppm | 9519 ppm |
| R-130a | N.D. | 685 ppm | 716 ppm | 434 ppm |

*Analyses may be unreliable due to high volatility
Vinylidene chloride clearly is reduced to very low levels by the process of the invention. It should be noted that relatively little R-141b is converted to R-131a so that the product yield loss is considered minimal. Some of the R-131a is probably converted further to R-110 and R-120, not shown in the above table.

EXAMPLE 2

The photochlorination of HCFC-141b was carried out in the same experimental apparatus used in Example 1. Two feed streams were passed separately through capillaries to pre-heat them to 60° C., then mixed and passed into the reactor at 135 kPa. The impure HCFC-141b contained the impurities listed in the table below. One stream contained no chlorine, while the second contained 0.198 mol/kg chlorine. By blending the two streams, the ratio of chlorine to vinylidene chloride was varied. Residence time in the reactor was determined by the sum of the two flow rates, and exposure was calculated from the residence time and the light intensity. After exposure to the ultraviolet light the product stream was condensed and analyzed by gas chromatography.

TABLE B

| Parameter | Feed | Sample 1 | Sample 2 | Sample 3 |
|---|---|---|---|---|
| $Cl_2$/V.C. molar ratio | — | 1.748 | 4.069 | 6.557 |
| Residence time (sec) | — | 22.16 | 18.85 | 27.45 |
| Exposure (w hr/kg) | — | 8.49 | 7.226 | 10.52 |
| Analytical Results | | | | |
| R-1131a | <10 ppm | <10 ppm | <10 ppm | <10 ppm |
| R-142b* | 402 ppm | 58 ppm | 77 ppm | 74 ppm |
| R-365 | 40 ppm | 38 ppm | 44 ppm | 41 ppm |
| R-1353 | 74 ppm | 28 ppm | <1 ppm | <1 ppm |
| Vinylidene chloride (R-1130a) | 779 ppm | 69 ppm | <10 ppm | <10 ppm |
| R-140a | 0.55% | 0.90% | 1.01% | 0.98% |
| trans-1,2-DCE | 10 ppm | <10 ppm | <10 ppm | <10 ppm |
| R-132b | N.D. | N.D. | N.D. | N.D. |
| R-131a | N.D. | 196 ppm | 1596 ppm | 2731 ppm |

TABLE B-continued

| Parameter | Feed | Sample 1 | Sample 2 | Sample 3 |
|---|---|---|---|---|
| R-130a | N.D. | 585 ppm | 703 ppm | 724 ppm |

*Analyses may be unreliable due to high volatility
It should be noted that in this example it is clear that other unsaturated compounds can also be removed by chlorination, i.e., R-1353 and trans-1,2-dichloroethylene (trans,-1,2-DCE).

EXAMPLE 3

The photochlorination of HCFC-141b was carried out in the same experimental apparatus used in Example 1. Two feed streams were passed separately through capillaries to pre-heat them to 60° C. then mixed and passed into the reactor at 135 kPa. The impure HCFC-141b contained the impurities listed in the table below. One stream contained no chlorine, while the second contained 0.372 mol/kg chlorine. By blending the two streams, the ratio of chlorine to vinylidene chloride was varied. Residence time in the reactor was determined by the sum of the two flow rates, and exposure was calculated from the residence time and the light intensity. After exposure to the ultraviolet light, the product stream was condensed and analyzed by gas chromatography.

TABLE C

| Parameter | Feed | Sample 1 | Sample 2 | Sample 3 |
|---|---|---|---|---|
| $Cl_2$/V.C. molar ratio | — | 1.73 | 4.31 | 6.89 |
| Residence time (sec) | — | 22.74 | 20.59 | 17.97 |
| Exposure (w hr/kg) | — | 8.72 | 7.89 | 6.89 |
| Analytical Results | | | | |
| R-1131a | <10 ppm | <10 ppm | <10 ppm | <10 ppm |
| R-142b* | 1.49% | 0.27% | 0.40% | 0.45% |
| R-365 | 40 ppm | 43 ppm | 44 ppm | 43 ppm |
| R-1353 | 74 ppm | 78 ppm | 5 ppm | <1 ppm |
| Vinylidene chloride | 779 ppm | 485 ppm | 45 ppm | <10 ppm |
| R-140a | 0.55% | 0.82% | 0.94% | 0.85% |
| trans-1,2-DCE | 10 ppm | 14 ppm | 13 ppm | <10 ppm |
| R-132b | N.D. | N.D. | 4 ppm | 17 ppm |
| R-131a | N.D. | 296 ppm | 1360 ppm | 5331 ppm |
| R-130a | N.D. | 575 ppm | 849 ppm | 831 ppm |

*Analyses may be unreliable due to high volatility
In the above table it may be noted that where the quantity of R-142b is quite large some R-132b is detected, although in very small amounts. Even where the severity of the chlorination is high as in Sample 3 only 17 wt. ppm of R-132b was detected. With the equipment used in these experiments, the limit of detectability of R-132b was about 1 wt. ppm.

EXAMPLE 4

The photochlorination of HCFC-141b was carried out in the same experimental apparatus used in Example 1 except that the two feed streams consisted of (1) impure R-141b, and (2) pure chlorine. The two feed streams were passed separately through capillaries to pre-heat them to 60° C., then mixed and passed into the reactor at 135 kPa. The impure HCFC-141b contained the impurities listed in the table below. By varying the flow rate ratio for the two streams, the ratio of chlorine to vinylidene chloride was varied. Residence time in the reactor was determined by the sum of the two flow rates, and exposure was calculated from the residence time and the light intensity. After exposure to the ultraviolet light, the product stream was condensed and analyzed by gas chromatography.

TABLE D

| Parameter | Feed | Sample 2 | Sample 3 | Sample 4 | Sample 5 | Sample 6 |
|---|---|---|---|---|---|---|
| $Cl_2$/V.C. molar ratio | — | 1.494 | 2.12 | 3.06 | 3.52 | 4.96 |
| Residence time (sec) | — | 12.13 | 10.34 | 9.33 | 8.57 | 9.29 |
| Exposure (w hr/kg) | — | 3.00 | 2.56 | 2.31 | 2.12 | 2.30 |
| Analytical Results | | | | | | |
| R-1131a (ppm) | <10 | <10 | <10 | <10 | <10 | <10 |
| R-142b* (ppm) | 402 | 222 | 253 | 222 | 232 | 228 |
| R-365 (ppm) | 40 | 44 | 47 | 45 | 41 | 44 |
| R-1353 (ppm) | 74 | 19 | 4 | <1 | <1 | <1 |
| Vinylidene chloride (ppm) | 779 | 54 | <10 | <10 | <10 | <10 |
| R-140a (%) | 0.55 | 0.61 | 0.71 | 0.83 | 0.75 | 0.83 |
| trans-1,2-DCD (ppm) | 10 | <10 | <10 | <10 | <10 | <10 |
| R-132b (ppm) | N.D. | N.D | N.D. | N.D | N.D. | N.D |
| R-131a (ppm) | 100 | 1232 | 1973 | 2661 | 4631 | 6169 |
| R-130a (ppm) | N.D. | 395 | 836 | 1223 | 1678 | 1695 |

It can be seen in the above table that the $Cl_2$/VC ratio may be increased and the UV exposure reduced to compensate so that similar results may be obtained.

We claim:

1. A process for selectively removing vinylidene chloride and other unsaturated compounds from 1,1-dichloro-1-fluoroethane with minimal loss of said 1,1-dichloro-1-fluoroethane comprising
   (a) contacting a gaseous mixture consisting substantially of 1,1-dichloro-1-fluoroethane and up to about 2000 wt. ppm vinylidene chloride with about 1-6 mols of chlorine for each mol of vinylidene chloride in the presence of ultraviolet light having wavelength between about 300 and 400 nm providing an exposure grater than zero and up to about 50 watts-hour/kg of said mixture, thereby reducing the concentration of vinylidene chloride to less than 200 wt. ppm by converting said vinylidene chloride to 1,1,1,2-tetrachloroethane; and
   (b) separating the 1,1,1,2-tetrachloroethane formed in (a) from 1,1-dichloro-1-fluoroethane.

2. The process of claim 1 wherein said 1,1-dichloro-1-fluoroethane contains up to 4 wt. % of 1-chloro-1,1-difluoroethane with formation of no more than about 20 wt. ppm of 1,2-dichloro-1,1-difluoroethane.

3. The process of claim 1 wherein said ultraviolet light provides an exposure of about 0.05 to 50 watts-hour/kg of said mixture.

4. The process of claim 1 wherein the contacting of (a) is carried out at a temperature of about 0° to 100° C.

5. The process of claim 1 wherein the concentration of vinylidene chloride is reduced to below 10 wt. ppm.

6. The process of claim 1 wherein the separation of (b) is carried out by distillation.

* * * * *